United States Patent [19]

La Zonby

[11] Patent Number: 5,368,749

[45] Date of Patent: Nov. 29, 1994

[54] SYNERGISTIC ACTIVITY OF GLUTARALDEHYDE IN THE PRESENCE OF OXIDANTS

[75] Inventor: Judy G. La Zonby, Crystal Lake, Ill.

[73] Assignee: Nalco Chemical Company, Naperville, Ill.

[21] Appl. No.: 243,026

[22] Filed: May 16, 1994

[51] Int. Cl.$^5$ .............................................. C02F 1/50
[52] U.S. Cl. .................................. 210/756; 210/759; 210/764; 210/928; 162/161; 162/199
[58] Field of Search ............... 210/764, 754, 759, 928, 210/756; 162/161, 199; 422/28, 56, 37; 514/705

[56] References Cited

U.S. PATENT DOCUMENTS

| | | |
|---|---|---|
| 4,455,287 | 6/1984 | Primack et al. ..................... 210/764 |
| 4,539,071 | 9/1985 | Clifford et al. . |
| 4,802,994 | 2/1989 | Mouché et al. . |
| 4,929,365 | 5/1990 | Clark et al. . |
| 5,061,373 | 10/1991 | Gallup ................................. 210/764 |
| 5,128,051 | 7/1992 | Theis et al. . |
| 5,198,453 | 3/1993 | La Zonby et al. . |
| 5,209,824 | 5/1993 | La Zonby et al. . |
| 5,324,432 | 6/1994 | Robertson et al. ................. 210/764 |

*Primary Examiner*—Neil McCarthy
*Attorney, Agent, or Firm*—Robert A. Miller; James J. Drake

[57] ABSTRACT

The present invention provides a composition and method of administering same for inhibiting the growth of aerobic microorganisms. The composition of the present invention includes sufficient amounts of an oxidant and glutaraldehyde. The method of the present invention includes the step of adding the oxidant and glutaraldehyde to industrial process waters.

3 Claims, No Drawings

SYNERGISTIC ACTIVITY OF GLUTARALDEHYDE IN THE PRESENCE OF OXIDANTS

BACKGROUND OF THE INVENTION

1. Field of the Invention

The present invention relates generally to controlling the growth of microorganisms. More specifically, the present invention relates to the use of compositions for inhibiting the growth of microorganisms in industrial waters.

2. Description of the Prior Art

The presence of microorganisms in waters, especially industrial waters, is a never-ending concern for industrial manufacturers. Examples of industrial waters where microorganisms can interfere with industrial processes include: cooling tower waters; mining process waters; food processing waters; sugar reprocessing waters; and the like.

In the paper industry, the growth of microorganisms in pulp and paper mill waters can adversely affect finished paper products. Microbial life depends on the nutrient supply, the pH and the temperature of a particular system. The warm temperatures and rich carbohydrate containing fluids of paper machines and process streams provide ideal growth conditions for a variety of microorganism. These contaminating microorganisms are capable of causing spoilage of pulp, furnish, or chemical additives. The microorganisms cause deposits that break loose and fall into the paper furnish, resulting in quality loss and/or end product defects such as holes and spots. The end result is unsalable paper or paper sold at a lower value.

The presence of microorganisms within industrial water systems results in the formation of deposits of biological origin on industrial machines. These formation deposits give rise to corrosion, breaks, increased down time, loss of yield, high chemical costs, odors and expensive deposit control programs. In the paper mill industry, slime deposit is reportedly responsible for nearly 70% of all breaks, blockages and pump failures.

Slime may be defined as an accretion or accumulation caused by certain micro-organisms in the presence of pulp fiber, filler, dirt and other materials, mixed in varied proportions, having variable physical characteristics and accumulating at continuous changing rates. In most industrial process waters, especially pulp and paper mill systems, spore forming bacteria and *Pseudomonas aeruginosa* contribute to slime formation. The later is most prevalent in paper mill slimes. Fungi is also a contributor toward slime formation.

The conventional method of controlling microbial growth is through the use of biocides. Biocides are generally divided into two main groups: oxidizing and non-oxidizing. These biocides act on the microorganisms by attacking them in one of three ways: by attacking the cell wall; the cytoplasmic membrane; or the cellular constituents.

One method is embodied in U.S. Pat. No. 4,802,994 issued Feb. 7, 1989 to Mouché, et al. The Mouché reference teaches the use of a composition containing hydrogen peroxide and glutaraldehyde to industrial process water to control the growth of microorganisms. However, the Mouché reference is specifically designed to counteract the growth of anaerobic organisms. Such a use of oxidants to counteract anaerobic organisms is appropriate since oxidants are toxic to anaerobic organisms as a result of the oxygen contained within them. Oxygen is, by nature, toxic to anaerobes. Aerobic organisms, in contrast, require oxygen in order to survive. As a result, no attempt has been made to use oxidants as an effective method of controlling the growth of aerobic microorganisms.

While biocides do inhibit microbial growth, economic and environmental concerns require improved methods. A problem with the use of biocides is that high levels of expensive chemicals are needed to control microbial growth. To date, none of the commercially available biocides have exhibited a prolonged biocidal effect. Their effectiveness is rapidly reduced as a result of exposure to physical stresses such as temperature or association with ingredients contained by the system toward which they exhibit an affinity. This results in a reduction or elimination of their biocidal effectiveness. Therefore, the use of such biocides involves continuous or frequent additions to paper mill systems. Further, these additions must be made at a plurality of points or zones in the system. The costs of the biocides and the labor costs involved are considerable.

Moreover, such chemicals are highly toxic in the quantities known to be required for effective control of microbial populations. As a result, environmental regulations restrict the amount of biocides that can safely be discarded into the environment. Therefore, a need exists for improved methods for controlling the growth of microorganisms in industrial process waters.

SUMMARY OF THE INVENTION

The present invention discloses a method for inhibiting the growth of aerobic microorganisms without the use of high levels of a biocide such as glutaraldehyde. The present invention further provides a composition for inhibiting the growth of aerobic microorganisms in industrial process waters that includes sufficient amounts of an oxidant and glutaraldehyde. The compositions of the present invention possess unexpected synergistic activity against aerobic microorganisms, including bacteria and fungi.

The present invention also provides a method for inhibiting the growth of the aerobic microorganisms in industrial process waters. The method includes the step of adding to the waters sufficient amounts of an oxidant and glutaraldehyde to enhance the effectiveness of the glutaraldehyde at lower dosage levels.

In one embodiment, the oxidant is selected from the group consisting of chlorine, bromine, potassium monopersulfate, sodium perborate, hydrogen peroxide, peracetic acid and sodium percarbonate.

In the preferred embodiment, the oxidant is added prior to the addition of the glutaraldehyde in the water system.

An advantage of the present invention is that it provides an improved method for inhibiting the growth of aerobic microorganisms.

Another advantage of the present invention is that it lowers the level of expensive chemicals needed for inhibiting the growth of aerobic microorganisms. With the addition of an oxidant in the water system, the glutaraldehyde is effective in low dosages, and as a result is long lasting. The increased effectiveness removes the need for repetitive additions of the glutaraldehyde at multiple points in the paper making system. Moreover, it provides a more environmentally friendly method for inhibiting the growth of aerobic microorganisms.

DESCRIPTION OF THE PREFERRED EMBODIMENTS

The present invention provides, for inhibiting the growth of aerobic microorganisms, improved compositions and method of administering same to a fluid system. The compositions include a sufficient amount of an oxidant and glutaraldehyde. It is well known that oxidants, since they contain oxygen, are toxic to anaerobic organisms. However, the compositions of the present invention are directed toward a method of controlling the growth of aerobic microorganisms.

The oxidant component of this invention includes oxidants that exhibit a synergistic effect when added to glutaraldehyde. Examples of suitable oxidants include: chlorine; hydrogen peroxide; peracetic acid; and sodium percarbonate.

The oxidants can be obtained from a number of chemical suppliers such as American Cyanamid, Buckman, Betz, Dearborn Chemical, Economics Laboratory, Inc., Merck, Nalco Chemical Company, and Vineland Chemical. The glutaraldehyde can be obtained from Union Carbide.

The combination of an oxidant along with the glutaraldehyde provides an unexpected synergistic relationship. The synergistic relationship is present in that the cooperative action of the combined oxidant with the glutaraldehyde yields a total effect which is greater than the sum of the effects of the oxidant or the glutaraldehyde taken separately.

The optimal amounts of oxidant and glutaraldehyde required for effectiveness in this invention depend on the type industrial waters being treated. In addition, the concentration of the combined components varies greatly and can depend upon conditions such as temperature and pH of the waters, and the microbial count. With respect to the oxidant, the lower and upper limits of the required concentration substantially depend upon the specific oxidant or combination of oxidants used. In one embodiment, the method comprises adding approximately 1 to 250 ppm of the oxidant along with approximately 5 to 500 ppm of the glutaraldehyde.

Since the suitable biocides that may be used in the present invention are often obtained at different usable concentrations, i.e. activity level, the ratios vary depending on the particular oxidant combined with the glutaraldehyde. For example, the peracetic acid used in the examples below is 5% active, the glutaraldehyde is 50% active, and the oxone is 43% active. Thus, a 1:1 ratio of PAA:Glut translates to 1:10 on an actives basis, while a 1:1 ratio of Oxone:Glut translates to almost 1:1 based on actives.

By way of example, the following are oxidants, including the percent of active ingredient, that may be used in the present invention: potassium monopersulfate (43% a.i.); peracetic acid (5% a.i.); hydrogen peroxide (30% a. a.i.); sodium perborate (53% a.i.), wherein "a.i." represents "active ingredient". The concentrations of hypochlorous acid and hypobromous acid are dependent upon the form by which they are added to the system, i.e. $Cl_2$ gas, NaOCl, etc. and the pH of the system.

Pursuant to the method of the present invention, the growth of aerobic microorganisms in industrial process waters can be inhibited. The method comprises the step of adding to the waters sufficient amounts of the oxidant and the glutaraldehyde of the present invention. In one embodiment, the oxidant and the glutaraldehyde are separate components that are added to the system.

In a preferred embodiment, the oxidant is added to the industrial water prior to the addition of the glutaraldehyde biocide. The oxidant can be added pursuant to any known method that provides the desired concentration of the same in the waters.

The following examples illustrate the synergistic relationship obtained with the compositions of the present invention.

Synergy is mathematically demonstrated by the industry accepted method described by S. C. Kull et al. in *Applied Microbiology*, vol. 9, pages 538–541 (1961). As applied to this invention, it is as follows:

$Q_A$ = the ppm of active glutaraldehyde alone which produces an endpoint.

$Q_B$ = the ppm of active oxidant alone which produces an endpoint.

$Q_a$ = the ppm of active glutaraldehyde, in combination, which produces an endpoint.

$Q_b$ = the ppm of active oxidant in combination, which produces an endpoint $$\frac{Q_a}{Q_A} + \frac{Q_b}{Q_B} = \text{Synergy index}$$

if Synergy Index (SI) is:
- $< 1$, it indicates synergy
- $= 1$, it indicates additivity
- $> 1$, it indicates antagonism The following test procedures were utilized during the experimentation of the present invention.

Process water from several papermills was obtained for test purposes. Aliquots of water from each mill were dosed with the indicated concentrations of oxidant. After 30 minutes of contact time, the designated concentrations of glutaraldehyde were added to the aliquots previously dosed with oxidant, mixed well and incubated at 37° C. in an orbital shaker. At the designated contact times, each aliquot was sampled to determine the total number of viable organisms in colony forming units per milliliter (CFU/mL) on Tryptone glucose Extract (TGE) agar. An endpoint of 2,3,4 or 5 $log_{10}$ reduction in viable organisms was then selected for calculating synergy.

EXAMPLE 1

Glutaraldehyde and Hydrogen Peroxide activity in papermill Process water, pH=7.4

| Biocide (ppm of a.i.) | Contact times | |
|---|---|---|
| | 1 Hour | 24 Hour |
| $H_2O_2$ - 25 | $1.2 \times 10^5$ | $1.8 \times 10^6$ |
| $H_2O_2$ - 50 | $4.6 \times 10^3$ | $<10^1$ |
| | 30 min | |
| Glut - 25 | $8.0 \times 10^2$ | $3.3 \times 10^6$ |
| Glut - 50 | $<10^1$ | $2.8 \times 10^6$ |
| Glut - 100 | $<10^1$ | $<10^1$ |
| $H_2O_2$ - 25/Glut - 25 | $1.0 \times 10^3$ | $<10^1$ |
| Control | $1.3 \times 10^5$ | $5.6 \times 10^5$ |

Synergy Calculation:

After 24 hours of contact, to achieve a $<10^1$ reduction, $Q_A$ = 100 (ppm of Glut alone)
$Q_B$ = 50 (ppm of $H_2O_2$ alone)
$Q_a$ = 25 (ppm of glut in combination)

$Q_b = 25$ (ppm of $H_2O_2$ in combination)

$$\frac{25}{100} + \frac{25}{50} = 0.75 = SI$$

EXAMPLE 2

Glutaraldehyde and Hydrogen Peroxide activity in Papermill Whitewater, pH=7.1

| Biocide (ppm of a.i.) | Contact times | |
| --- | --- | --- |
| | 1 Hour | 24 Hour |
| $H_2O_2$ - 25 | $7.2 \times 10^5$ | $9.2 \times 10^6$ |
| $H_2O_2$ - 50 | $3.3 \times 10^5$ | $3.9 \times 10^6$ |
| | 30 min | |
| Glut - 25 | $4.0 \times 10^3$ | $9.3 \times 10^5$ |
| Glut - 50 | $1.2 \times 10^3$ | $2.2 \times 10^3$ |
| Glut - 100 | $7.7 \times 10^2$ | $2.2 \times 10^2$ |
| $H_2O_2$ - 10/Glut - 75 | $2.8 \times 10^3$ | $<10^1$ |
| Control | $4.0 \times 10^6$ | $8.6 \times 10^6$ |

Synergy Calculation:

After 24 hours of contact, to achieve a $<10^1$ reduction, $Q_A = >100$ (200) ppm of Glut alone
$Q_B = >50$ (100) ppm of $H_2O_2$ alone
$Q_a = 75$ ppm of Glut in combination
$Q_b = 10$ ppm of $H_2O_2$ in combination $$\frac{75}{200} + \frac{10}{100} = 0.475 = SI$$

EXAMPLE 3

Glutaraldehyde and Peracetic Acid activity in Papermill Whitewater, pH=7.0

| Biocide (ppm of a.i.) | Contact times | |
| --- | --- | --- |
| | 1.5 Hour | 24 Hour |
| PAA - 5 | $2.9 \times 10^6$ | $6.1 \times 10^6$ |
| PAA - 10 | $4.0 \times 10^6$ | $6.4 \times 10^6$ |
| PAA - 20 | $9.3 \times 10^5$ | $6.5 \times 10^5$ |
| | 1 Hour | |
| Glut - 10 | $2.8 \times 10^6$ | $9.5 \times 10^2$ |
| Glut - 20 | $7.2 \times 10^5$ | $1.1 \times 10^2$ |
| Glut - 40 | $3.2 \times 10^4$ | $<10^1$ |
| PAA - 10/Glut - 10 | $3.2 \times 10^5$ | $1.9 \times 10^2$ |
| PAA - 20/Glut - 20 | $2.9 \times 10^3$ | $<10^1$ |
| Control | $2.3 \times 10^6$ | $5.0 \times 10^6$ |

Synergy Calculation:

After 1 Hour of Glutaraldehyde contact, a 3 log reduction is achieved, $Q_A = >40$ (80) ppm of Glut alone
$Q_B = >20$ (40) ppm of PAA alone
$Q_a = 20$ ppm of Glut in combination
$Q_b = 20$ ppm of PAA in combination $$\frac{20}{80} + \frac{20}{40} = 0.75 = SI$$

After 24 hours of contact, to achieve a 4 log reduction, $Q_A = 20$ ppm of Glut alone
$Q_B = >20$ (40) ppm of PAA alone
$Q_a = 10$ ppm of Glut in combination
$Q_b = 10$ ppm of PAA in combination $$\frac{10}{20} + \frac{10}{40} = 0.75 = SI$$

EXAMPLE 4

Glutaraldehyde and Hypochlorous Acid activity in Papermill Whitewater, pH=7.1

| Biocide (ppm of a.i.) | Contact times | |
| --- | --- | --- |
| | 1 Hour | 24 Hour |
| HOCl* - 0.5 | $3.1 \times 10^6$ | $4.2 \times 10^6$ |
| HOCl - 1.0 | $2.9 \times 10^6$ | $1.4 \times 10^6$ |
| HOCl - 2.0 | $5.3 \times 10^3$ | $1.7 \times 10^6$ |
| | 0.5 Hour | |
| Glut - 10 | $3.5 \times 10^6$ | $6.8 \times 10^6$ |
| Glut - 20 | $4.3 \times 10^5$ | $4.2 \times 10^6$ |
| Glut - 40 | $2.5 \times 10^4$ | $1.3 \times 10^4$ |
| HOCl - 0.5/Glut - 40 | $5.9 \times 10^3$ | $2.7 \times 10^2$ |
| Control | $1.6 \times 10^7$ | $9.8 \times 10^5$ |

*HOCl measured as ppm of $Cl_2$ by DPD methodology

Synergy Calculation:

After 0.5 Hour of Glutaraldehyde contact, a reduction to $10^3$ is achieved by, $Q_A = >40$ (80) ppm of Glut alone
$Q_B = 2.0$ ppm of HOCl alone
$Q_a = 40$ ppm of Glut in combination
$Q_b = 0.5$ ppm of HOCl in combination $$\frac{40}{80} + \frac{0.5}{2.0} = 0.75 = SI$$

After 24 hours of contact, to reduction to $10^2$ is achieved by, $Q_A = >40$ (80) ppm of Glut alone
$Q_B = >2.0$ ppm of HOCl alone
$Q_a = 40$ ppm of Glut in combination
$Q_b = 0.5$ ppm of HOCl in combination $$\frac{40}{80} + \frac{0.5}{4.0} = 0.625 = SI$$

EXAMPLE 5

Glutaraldehyde and Potassium monopersulfate (Oxone) activity in Papermill Whitewater, pH=7.1

| Biocide (ppm of a.i.) | Contact times | |
| --- | --- | --- |
| | 1 Hour | 24 Hour |
| Oxone - 25 | $3.7 \times 10^5$ | $3.9 \times 10^5$ |
| Oxone - 50 | $1.6 \times 10^5$ | $8.1 \times 10^4$ |
| Oxone - 100 | $6.4 \times 10^2$ | $<10^1$ |
| | 0.5 Hour | |
| Glut - 25 | $4.9 \times 10^4$ | $1.8 \times 10^5$ |
| Glut - 50 | $2.4 \times 10^2$ | $1.6 \times 10^2$ |
| Glut - 100 | $3.8 \times 10^2$ | $4.2 \times 10^2$ |
| Oxone - 25/Glut - 25 | $5.5 \times 10^2$ | $2.2 \times 10^2$ |
| Control | $6.0 \times 10^5$ | $4.8 \times 10^6$ |

Synergy Calculation:

After 0.5 Hour of Glutaraldehyde contact, a reduction to $10^2$ is achieved by, $Q_A = 50$ ppm of Glut alone
$Q_B = 100$ ppm of Oxone alone
$Q_a = 25$ ppm of Glut in combination
$Q_b = 25$ ppm of Oxone in combination $$\frac{25}{30} + \frac{25}{100} = 0.75 = SI$$

After 24 hours of contact, a reduction to $10^2$ is achieved by,
$Q_A = 50$ ppm of Glut alone
$Q_B = 100$ ppm of Oxone alone
$Q_a = 25$ ppm of Glut in combination
$Q_b = 25$ ppm of Oxone in combination $$\frac{25}{30} + \frac{25}{100} = 0.75 = SI$$

It should be understood that various changes and modifications to the presently preferred embodiments described herein will be apparent to those skilled in the art. Such changes and modifications can be made without departing from the spirit and scope of the present invention and without diminishing it attendant advantages. It is therefore intended that such changes and modifications be covered by the appended claims.

I claim:

1. A method for controlling the growth of aerobic microorganisms in industrial process water comprising the water of a pulp and paper mill system including the step of adding to the industrial water an amount of glutaraldehyde and an amount of an oxidant selected from the group consisting of hypochlorous acid, potassium monopersulfate, hydrogen peroxide, and peracetic acid, said amount of oxidant being in the range of from about 0.5 to about 250 ppm and said amount of glutaraldehyde being in the range of from about 5 to about 500 ppm, said amounts of oxidant and glutaraldehyde being selected to result in a synergy index of less than 1 wherein said synergy index is calculated by determining a first ratio of said amount of glutaraldehyde required to produce a level of microorganism growth control when added in combination with said amount oxidant to the amount of glutaraldehyde required to produce said level of growth control in the absence of said oxidant, and adding said first ratio to a second ratio of said amount of oxidant required to produce said level of microorganism growth control when added in combination with said amount of glutaraldehyde to the amount of oxidant required to produce said level of growth control in the absence of said glutaraldehyde.

2. The method of claim 1, wherein the aerobic microorganisms contain bacteria.

3. The method of claim 1, wherein the oxidant is added to the industrial water prior to the addition of the glutaraldehyde.

* * * * *